(12) United States Patent
Arai et al.

(10) Patent No.: US 6,243,439 B1
(45) Date of Patent: Jun. 5, 2001

(54) CT SCANNING APPARATUS (75) Inventors: Yoshinori Arai, Tokyo; Masakazu Suzuki, Kyoto, both of (JP)

(73) Assignee: Kabushiki Kaisha Morita Seisakusho, Kyoto (JP)

( * ) Notice: Subject to any disclaimer, the term of this patent is extended or adjusted under 35 U.S.C. 154(b) by 0 days.

(21) Appl. No.: 09/265,908

(22) Filed: Mar. 10, 1999

(30) Foreign Application Priority Data

Mar. 11, 1998 (JP) ................................... 10-080296

(51) Int. Cl.$^7$ ....................................................... A61B 6/03
(52) U.S. Cl. ................. 378/20; 378/8; 378/162; 378/205; 378/207
(58) Field of Search ........................... 378/4, 8, 20, 191, 378/901, 162, 163, 164, 207

(56) References Cited

U.S. PATENT DOCUMENTS

| | | | |
|---|---|---|---|
| 4,710,875 * | 12/1987 | Nakajima et al. | 378/162 |
| 4,860,331 * | 8/1989 | Williams et al. | 378/163 |
| 5,109,397 * | 4/1992 | Gorden et al. | 378/205 |
| 5,416,822 * | 5/1995 | Kunik | 378/162 |
| 5,442,674 * | 8/1995 | Picard et al. | 378/20 |
| 5,636,255 * | 6/1997 | Ellis | 378/20 |
| 5,872,829 * | 2/1999 | Wischmann et al. | 378/164 |
| 6,038,282 * | 3/2000 | Wiesent et al. | 378/62 |
| 6,044,132 * | 3/2000 | Navab | 378/163 |
| 6,049,582 * | 4/2000 | Navab | 378/4 |
| 6,148,058 * | 11/2000 | Dobbs | 378/19 |

* cited by examiner

Primary Examiner—Robert H. Kim
Assistant Examiner—Allen C Ho
(74) Attorney, Agent, or Firm—Koda & Androlia (57) ABSTRACT A CT scanning apparatus in accordance with the present invention comprises an image pickup system having an X-ray source being rotated around an object and a two-dimensional X-ray image pickup portion disposed opposite to the X-ray source with the object therebetween and being rotated, and is configured to rotate the image pickup system so as to radiograph three-dimensional areas inside the object, wherein a substance capable of being detected as an X-ray image is used as a position marker, and the position marker is disposed so as to be positioned in the image pickup view of the image pickup system during the rotation of the image pickup system and radiographed together with the object. In an ideal case, the image of the position marker in the two-dimensional X-ray image obtained as described above moves in a sine curve. Therefore, a correction amount for each X-ray image is calculated from the difference between the actual position in the X-ray image and the ideal position changing in the sine curve. By using the correction amount, the two-dimensional X-ray image is corrected, and a CT image is built. As a result, the effects of "moving artifact" and the like can be eliminated, and a clear image can be obtained.

8 Claims, 10 Drawing Sheets

CT SCANNING APPARATUS

BACKGROUND OF THE INVENTION

1. Field of the Invention

The present invention relates to a CT scanning apparatus, and more particularly to a partial CT scanning apparatus suitable for partially radiographing tooth, jaw and face areas, for example.

2. Description of the Prior Art

A CT scanning apparatus generally comprises an X-ray source moving along a circular orbit around an object and an X-ray image pickup portion moving along a circular orbit on the opposite side of the X-ray source with respect to the object. In the image pickup portion, a line sensor arranged in a line or in a circular orbit detects X-rays passing through the object, and an X-ray image is built. In addition to this type of apparatus, an apparatus for carrying out radiographing by using a spiral orbit while an object placed on a bed is moved, and an apparatus for radiographing three-dimensional areas by using a two-dimensional image sensor, such as a TV camera, in its image pickup portion are also known.

In the case of these apparatuses, a blurred image is generated because of displacements of the X-ray source and the X-ray image pickup portion from their original orbits and movement of the object, even if the resolution of the image pickup system is raised. If the displacements from the orbits occur in the same pattern, the displacements can be corrected on the basis of the pattern when the image is built. However, if the displacements do not occur in the same pattern, correction is difficult. Furthermore, regarding the movement of the object, when the object is a living body in particular, the object itself may move during radiographing, and the so-called "moving artifact" occurs. To prevent this problem, the patient under test is required to be secured to a bed, for example. This further causes a problem of making the apparatuses larger in overall size.

SUMMARY OF THE INVENTION

Accordingly, a first object of the present invention is to provide a partial CT scanning apparatus for carrying out partial CT scanning to radiograph teeth, jaws and the like in particular, being capable of stably obtaining high-resolution images by improving image quality so that, in spite of displacements of the X-ray source and the X-ray image pickup portion from their original orbits, movement of the object and the like, the effects of these displacements can be eliminated by image processing. A second object of the present invention is to provide a partial CT scanning apparatus having the above-mentioned functions, and being compact in size and low in cost.

In order to attain the above-mentioned objects, the CT scanning apparatus of the present invention comprises an image pickup system having an X-ray source being rotated along a circular orbit around an object and a two-dimensional X-ray image pickup portion disposed opposite to the X-ray source with the object therebetween and being rotated along a circular orbit, and is configured to rotate the image pickup system so as to radiograph three-dimensional areas inside the object, wherein a substance capable of being detected as an X-ray image is used as a position marker, the position marker is disposed so as to be positioned in the image pickup view of the image pickup system during the rotation of the image pickup system and radiographed together with the object, a correction amount for each X-ray image is calculated from the position of the image of the position marker in an obtained two-dimensional X-ray image, the two-dimensional X-ray image is corrected by using the correction amount, and a CT image is built.

In an ideal case, the image of the position marker in the X-ray image obtained by radiographing moves in a sine curve. Therefore, the difference between the actual position in the X-ray image and the ideal position changing in the sine curve corresponds to displacements due to displacements from the orbits or movement of the object. Accordingly, the image of the position marker taken in the X-ray image is traced to obtain a correction amount in accordance with the position of the image, and the X-ray image is moved in parallel to carry out back projection. As a result, errors in the mechanical, electrical and other systems due to displacements of the image pickup system from original orbits and errors due to displacements caused by movement of the object during radiographing are all corrected in all the horizontal and vertical directions. The effects of "moving artifact" and the like can thus be eliminated, and a clear image can be built, whereby accurate diagnosis can be attained. Furthermore, the accuracy of the mechanical system of the apparatus may be lowered to some extent. Consequently, the apparatus can be made compact in size and low in cost, and can be calibrated easily.

Moreover, instead of radiographing the position marker together with the object as described above, only the position marker is radiographed before regular radiographing. From the position of the image of the position marker in the obtained two-dimensional X-ray image, it is possible to calculate error data regarding the image pickup system in each X-ray image. As a result, a two-dimensional X-ray image during regular radiographing can be corrected by using the data, whereby errors in the image pickup system can be eliminated. In addition, the data can also be used to find and remedy improper portions in the mechanical, electrical and other systems, which may cause errors.

Concrete configurations of the CT scanning apparatus in accordance with the present invention will be clarified by explanations regarding an embodiment described below.

DETAILED DESCRIPTION OF THE PREFERRED EMBODIMENTS

An embodiment of the present invention will be described below. First, the outline structure of the apparatus will be described.

Figure 1:
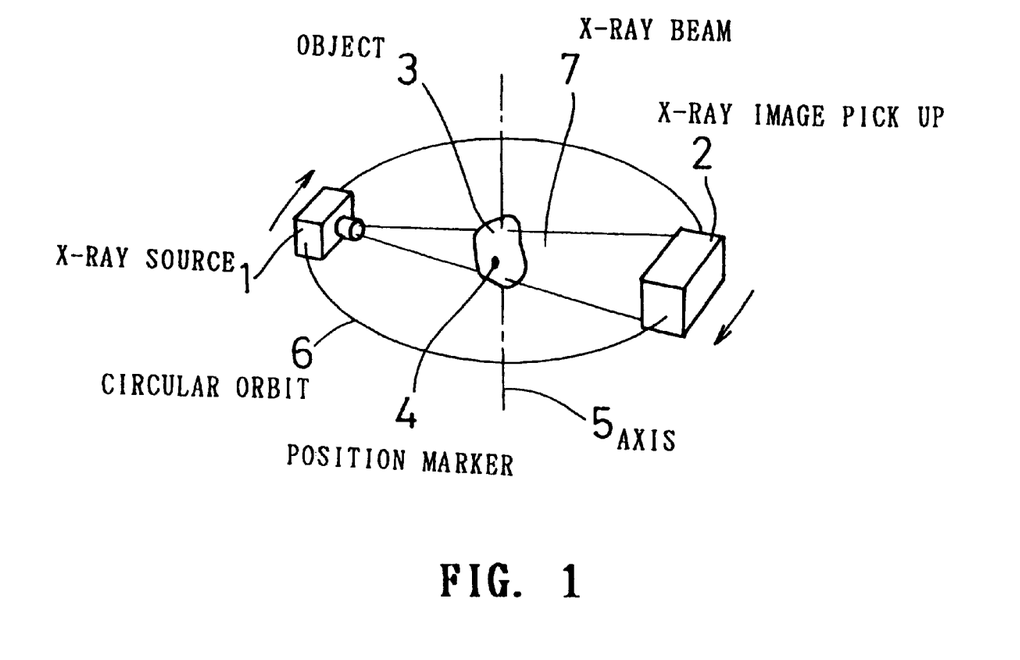
FIG. 1 is a view illustrating the relationship between the radiographing system and an object of the apparatus in accordance with the present invention.

Referring to FIG. 1, the numeral 1 represents an X-ray source, the numeral 2 represents a two-dimensional X-ray image pickup portion, the numeral 3 represents an object, the numeral 4 represents a position marker, the numeral 5 represents an axis line, the numeral 6 represents a circular orbit on a plane perpendicular to the axis line 5, and the numeral 7 represents an X-ray beam. The X-ray source 1 is disposed in an opposed relation with the two-dimensional Xray image pickup portion 2 with the object 3 disposed therebetween. The X-ray beam 7 is applied to the object 3 while the X-ray source 1 and the two-dimensional X-ray image pickup portion 2 rotate along the circular orbit 6. A target three-dimensional area inside the object 3 is radiographed during one rotation. The circular orbit along which the X-ray source 1 rotates is not required to be the same as the circular orbit along which the X-ray image pickup portion 2 rotates, but the circular orbits should only be concentric circles centered at the axis line 5.

Figure 2:
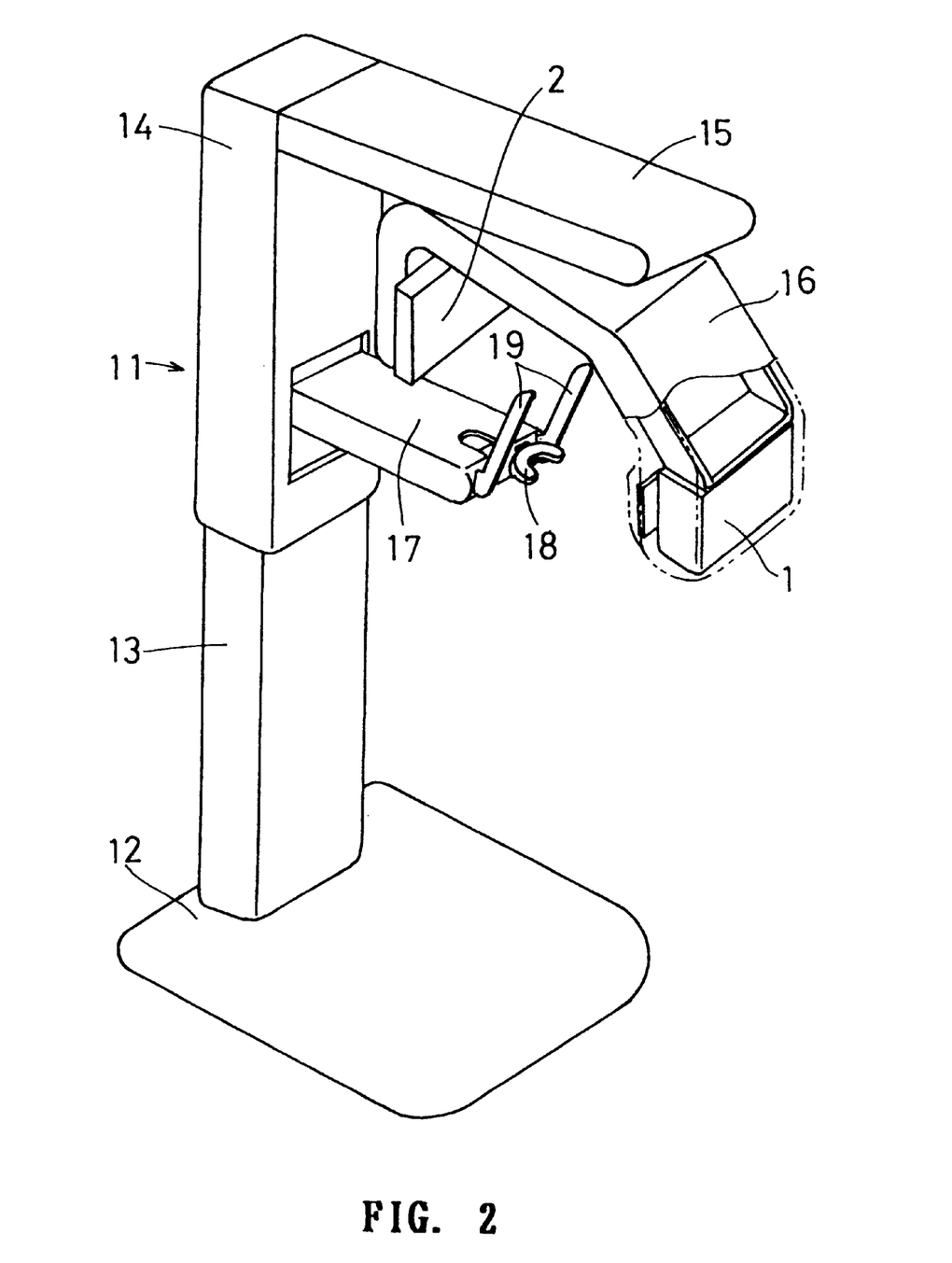
FIG. 2 is a perspective overall view showing the apparatus in accordance with an embodiment of the present invention.

FIG. 2 is a view showing an embodiment of an apparatus for radiographing human faces and heads as objects at dental, otolaryngologic and other clinics. Referring to FIG. 2, the numeral 11 represents an apparatus body. A column 13 stands on a base 12. A lift frame 14 is installed on the column 13 so as to be movable vertically. A rotary arm 16 is rotatably supported by a horizontal arm 15 provided at the upper end of the lift frame 14. The X-ray source 1 is installed at one end of the rotary arm 16, and the two-dimensional X-ray image pickup portion 2 is installed at the other end thereof. At the lower portion of the lift frame 14, an arm-shaped object position adjustment mechanism 17 is provided in parallel with the horizontal arm 15 so as to be movable vertically. The end portion of the arm-shaped object position adjustment mechanism 17 is positioned under the midpoint area between the X-ray source 1 and the two-dimensional X-ray image pickup portion 2. At the center of the end portion thereof, a bite block 18 is provided, and on each side of the end portion thereof, an ear rod 19 is provided.

The above-mentioned configuration is similar to and not much different from the configuration of a conventional dental panoramic radiographic apparatus except that the two-dimensional X-ray image pickup portion 2 is used instead of the film cassette in the X-ray detection portion of the conventional apparatus, that the bite block 18 is used instead of the chin rest of the conventional apparatus, and that the X-Y table for moving the rotary arm 16 of the conventional apparatus is omitted. With this configuration wherein the X-ray source and the X-ray image pickup portion are rotated along circular orbits on a horizontal plane, the apparatus can be used not only as a special-purpose apparatus for CT scanning but also as an apparatus for both CT scanning and panoramic radiographing by adding the functions of the panoramic radiographing apparatus to the apparatus of the present invention. With this configuration, the apparatus can be less complicated in structure and less in cost, and can be handled easily.

Furthermore, a control device for controlling the vertical movement of the lift frame 14 and the object position adjustment mechanism 17, the rotation of the rotary arm 16 and the operation of the image pickup system including the X-ray source 1 and the two-dimensional X-ray image pickup portion 2, peripheral attached circuits thereof, and the like can be configured appropriately so as to be similar to those of the conventional panoramic radiographing apparatus. Calculating a correction amount, correcting displacements and building a CT image in accordance with the present invention can be carried out by using a CPU and a memory provided in the above-mentioned control device, or can be processed by using an external computer. More detailed specific examples of the configuration and control circuits of the apparatus will be described later.

At the time of CT scanning, as a first step, the head of a patient is placed between the X-ray source 1 and the two-dimensional X-ray image pickup portion 2 just as in the case of panoramic radiographing. The patient stands on the base 12 or sits on a chair being electrically movable in the vertical direction, but not shown in FIG. 2. The position of the head is adjusted by the object position adjustment mechanism 17 so that a predetermined portion to be radiographed is positioned in the image pickup view of the X-ray image pickup portion 2. The ear rods 19, 19 are then used to hold the head on both sides thereof, and the patient bites the bite block 18 inserted into the mouth, whereby the head of the patient is secured.

Before starting radiographing by operating the image pickup system, the approximate position of the image of the position marker 4 picked up by the image pickup portion 2 in a two-dimensional X-ray image is detected. The placement of the position marker 4, the direction of the image pickup system and the like are set so that the image is positioned in the image pickup view during the rotation of the rotary arm 16 at all times. The approximate position of the position marker 4 is determined by the initial position of the marker 4 and the dimensions of the mechanical system of the apparatus.

The rotary arm 16 is then rotated while the X-ray source 1 and the two-dimensional X-ray image pickup portion 2 are operated. While the rotary arm 16 rotates one rotation, plural X-ray images of the patient's head used as an object are taken together with the image of the position marker 4 and recorded. Two-dimensional X-ray images recorded in this way are subjected to correction processing in accordance with the present invention, and a target CT image is built. The details of the correction processing will be described later. If the capability of the control device is large, the correction can be processed in real time while the two-dimensional X-ray image pickup is carried out.

Figure 3:
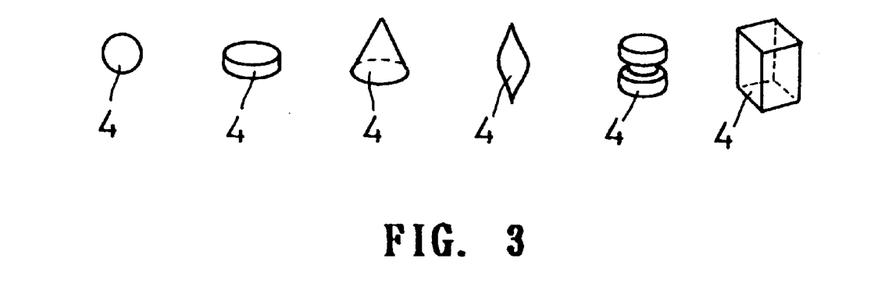
FIG. 3 perspectively shows the examples of the shape of the position marker used for the apparatus in accordance with the present invention.

The position marker 4 is made of a material, such as a metal, which can be detected as an X-ray image. Since it is desired that the image of the position marker 4 is unchanged in any directions and laterally symmetrical, a shape symmetrical with respect to the center line thereof, such as a body of revolution, is suitable. FIG. 3 shows examples of the shape of the position marker 4, that is, a sphere, a cylinder (or a disc), a cone, a spindle, a cylindrical body of revolution constricted at the middle thereof and a quadrangular prism symmetrical with respect to the center line thereof (not a body of revolution), from left to right.

By disposing the position marker 4 having one of these shapes so that the axis line thereof is parallel with the axis line 5 of the circular orbit 6, the marker 4 can be detected as the same image or laterally symmetrical images in any directions on the circular orbit 6. Therefore, a correction amount can be calculated easily. The size of the position marker 4 should preferably be about 4 mm or more in diameter in the case of a sphere, or about 4 mm or more in diameter and height in the case of a cylinder, for example. If the marker is too small, the accuracy at the position of the center of gravity thereof may lower at the time when the correction amount is obtained.

Figure 4A:
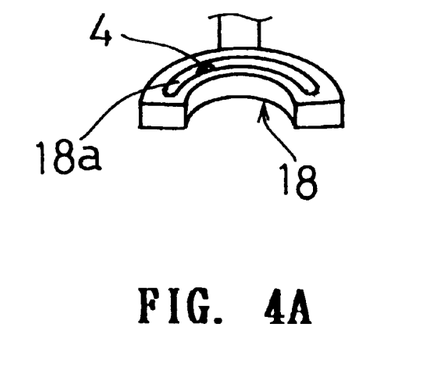
FIG. 4A is a perspective view showing a bite block in accordance with the embodiment of the present invention.
Figure 4B:
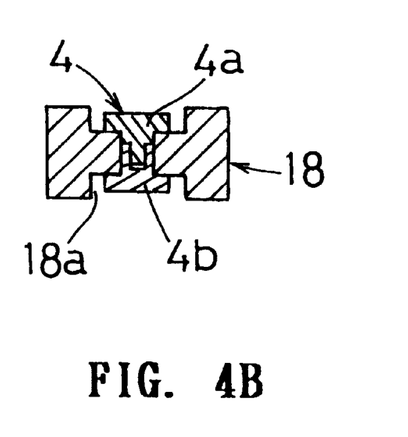
FIG. 4B is a sectional view showing the bite block.

The position marker 4 is required to be secured to an object so as not to move relative to the object during radiographing. As a securing means for this purpose, an appropriate device should be used. FIGS. 4A and 4B show an example embodied by using the bite block 18. More specifically, an arcuate slit 18$a$ is formed in the arcuate main body of the bite block 18, and the position marker 4 having a cylindrical shape constricted at the middle thereof shown in FIG. 3 is fitted in the slit 18$a$. The position marker 4 is designed to be moved in the slit 18$a$ by hand and to be held by a force to the extent that the marker 4 is not moved easily even when the marker makes contact with teeth in the mouth. This kind of bite block 18 should preferably be available in plural so as to be selectable depending on the size of the patient, such as the size of an adult or a child. The bite block 18 is formed of plastic or the like for example, which is an X-ray transmission material hardly detected as an X-ray image.

Slight arcuate projections and depressions having a diameter similar to the diameter of the axis portion of the marker may be formed along the inner rim of the slit 18$a$, whereby a click feeling can be obtained, the position marker 4 can be positioned easily, and an appropriate holding force can be obtained easily at a predetermined position. Instead of the above-mentioned slit 18$a$, plural holes may be provided so that the position marker 4 can be inserted into a desired hole. In dental diagnosis, CT scanning is usually carried out for a tooth (or teeth) and its peripheral area. In the case when the position marker 4 is embedded so as not to project beyond the upper and lower surfaces of the bite block 18 as shown in FIG. 4B, the image of a tooth (or teeth) and the image of the position marker 4 do not overlap each other. This type of marker is thus advantageous.

In FIG. 4B, the position marker 4 comprises an upper member 4$a$ and an lower member 4$b$. A male thread is provided on one of the members and a female thread is provided in the other member as mounting means for connection so that they can be threadedly engaged with each other. With this connection, the members are detachable as desired, and the installation position thereof can be changed easily. In this example, the position marker 4 has mounting means for installation to the bite block 18. However, briefly speaking, a means for securing the position marker 4 to the object should only be provided so that correction is carried out properly. This means can also be provided in the bite block 18 or the like other than the position marker.

Figure 5A:
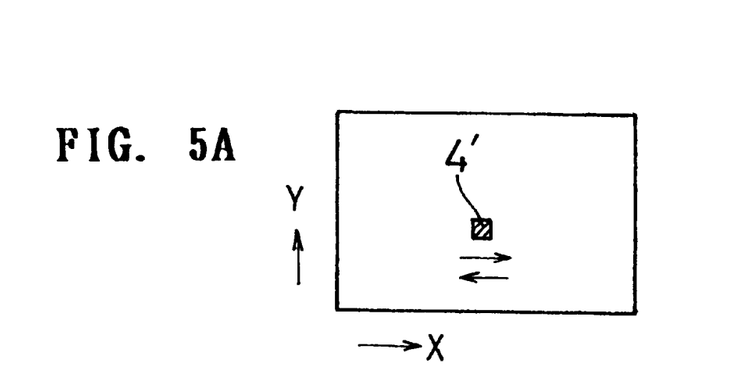
FIG. 5A is a view showing the image of the position marker in an X-ray image in accordance with the embodiment.

Next, the correction of a displacement will be described below. FIG. 5A shows the image 4' of the position marker 4 in an X-ray image obtained by one radiographing operation. The image 4' of the position marker 4 In the X-ray image is stationary, provided that the orbit of the X-ray source 1 and the orbit of the X-ray image pickup portion 2 are not displaced, and the position marker 4 having a shape of a body of revolution is disposed so that the axis line thereof completely coincides with the axis line 5 of the circular orbit 6. However, it is generally difficult to accurately dispose the position marker 4 on the axis line 5. In an ideal condition wherein there is no displacement in the image pickup system, the image 4' of the position marker moves right and left as indicated by arrows in FIG. 5A. This movement draws a sine curve indicated by a broken line in FIG. 5B. When it is assumed that the horizontal direction is the X-axis, the X-coordinate thereof changes along the curve of $\sin(\emptyset+\alpha)$.

Figure 5B:
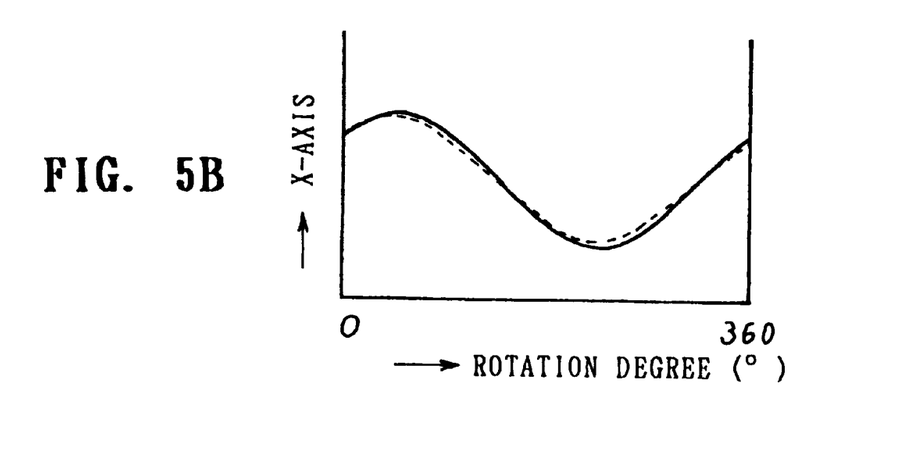
FIG. 5B is a graph showing the movement of the position marker.

On the other hand, in the case when the image pickup system is displaced or the object is moved, the image 4' of the position marker is moved along a curve indicated by a solid line shown in FIG. 5B away from the broken line indicating the ideal condition. Therefore, by correcting the position of the solid line by using the difference between the broken line and the solid line as an correction amount, an image with no displacement can be obtained. A procedure for correction will be described below in accordance with the flowchart of FIG. 6.

Figure 6:
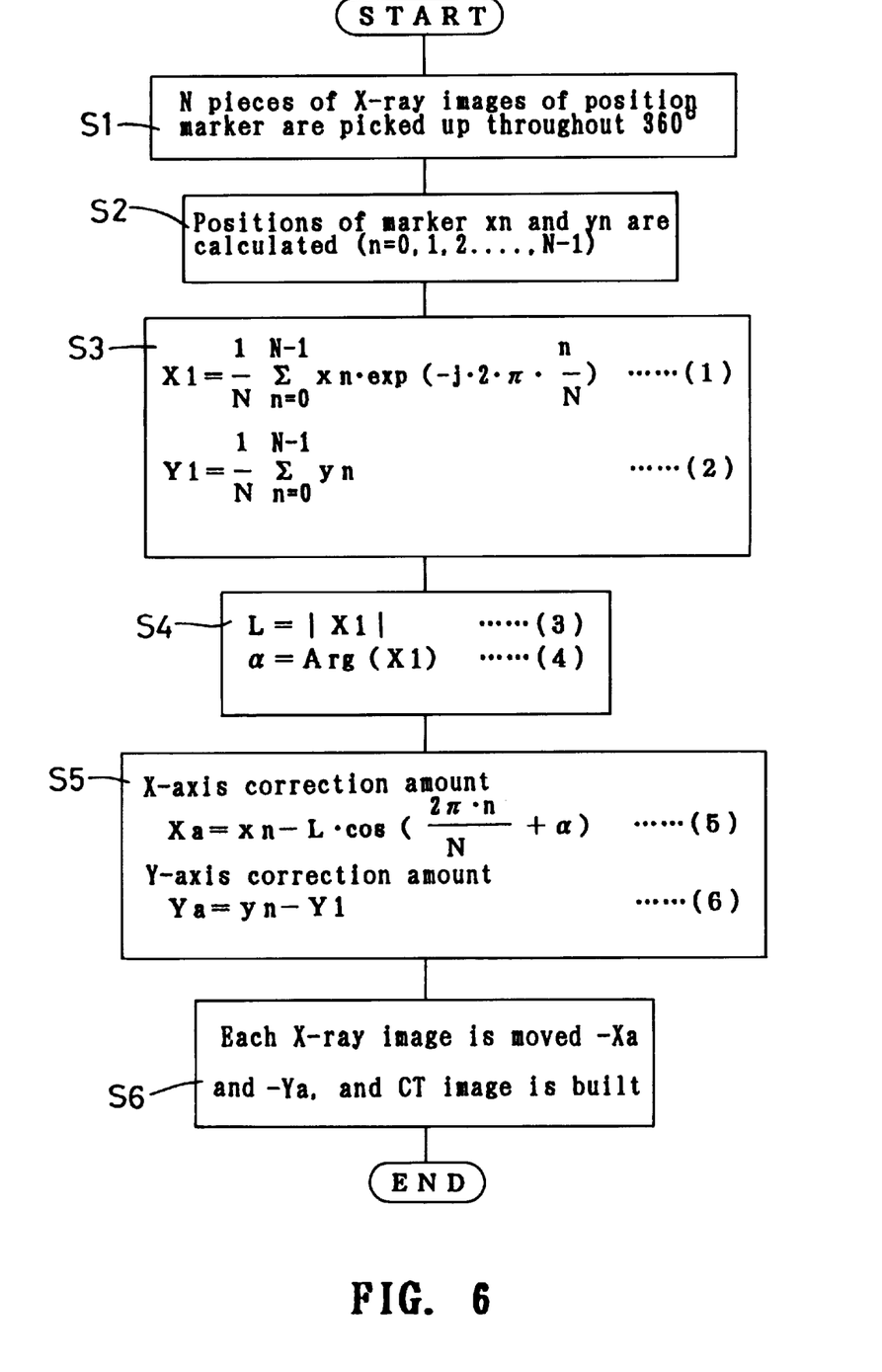
FIG. 6 is a flowchart showing a correction procedure in accordance with the embodiment.

Step S1 in FIG. 6 is a step wherein the rotary arm 16 is rotated while the X-ray source 1 and the two-dimensional X-ray image pickup portion 2 are operated, and plural two-dimensional X-ray images are picked up while the rotary arm 16 makes one rotation. The number of images to be picked up is assumed to be N. Next, at step S2, the position of the image 4' of the position marker in each X-ray image is detected. This position can be obtained by binary conversion of the image 4' and by obtaining the center of gravity thereof in the X-ray image.

When the position of the center of gravity is assumed to be function $f(\emptyset)$ of an angle, this can be ideally represented by $L \cdot \cos(\emptyset+\alpha)$. L is a constant determined by the distance between the center of gravity of the position marker 4 and the axis line 5. By using suffix n for identification, the position of the center of gravity of the image 4' in the N-th X-ray image can be represented by ($x_n$, $y_n$), and the x-coordinate of the center of gravity can be represented by $f(\emptyset_n)=x_n$. Furthermore, the y-coordinate of the center of gravity in the Y-axis direction (the direction of the axis line 5) is a constant in an ideal case. When $f(\emptyset_n)$ is subjected to Fourier transformation and the linear term thereof is taken, the term is just represented by $L \cdot \cos(\emptyset+\alpha)$. At step S3, X1 and Y1 are obtained by calculating equations (1) and (2), and at step S4, equations (3) and (4) are calculated. As a result, $f(\emptyset)=L \cdot \cos(\emptyset+\alpha)$ can be obtained in the case when there is no displacement, that is, in an ideal case.

Therefore, in the X-axis direction, by subtracting $f(\emptyset_n)$ in an ideal case at the angle of each X-ray image from the position $x_n$ of the center of gravity of the image 4' in each X-ray image in accordance with equation (5) at step S5, correction amount Xa required for the X-ray image can be obtained. Furthermore, in the Y-axis direction, by subtracting constant Y1 obtained from equation (2) at step S3 from the position $y_n$ of the center of gravity of the image 4' in each X-ray image in accordance with equation (6) at step S5, correction amount Ya required for the X-ray image can be obtained.

At step S6, by using these correction amounts, a two-dimensional image at each angle is moved in parallel by -Xa in the X-axis direction and also moved in parallel by -Ya in the Y-axis direction to build a CT image. As a result, displacements from the original orbits of the X-ray source 1 and the X-ray image pickup portion 2, displacements due to the movement of the object 3 and the like during radiographing can be corrected, whereby clear, three-dimensional CT images free from blurs can be obtained.

Instead of the above-mentioned processing, f(øn) is subjected to Fourier transformation, only the linear term of the result of the transformation is deleted, and the remainder is subjected to inverse Fourier transformation. The result thus obtained just exactly becomes a correction amount. Therefore, the correction amount in the X-axis direction can be obtained by this processing. Furthermore, although the coordinate in the Y-axis direction is assumed to be a constant in the above-mentioned example, the coordinate in the Y-axis direction can also be corrected just as in the case of the X-axis direction as a matter of course. With the present invention, the displacements of the image pickup system and the movement of the object in all directions can be corrected, whereby clear, three-dimensional CT images can be obtained.

Furthermore, to correct "moving artifact," the object and the position marker 4 are required to be radiographed simultaneously at the time of radiographing as described above. In the case of correcting errors in the mechanical, electrical or other systems, such as displacements in the image pickup system, by obtaining error data by radiographing only the position marker 4 before regular radiographing, and by using the data, the result of the regular radiographing can be corrected. In the case when only the position marker is radiographed as describe above, a rod measuring about 5 mm in diameter and about 40 mm in height is suitable as the position marker 4. Even if the position marker is disposed in a slightly inclined condition, no problem occurs in actual operation. The error data can also be used to find and remedy improper portions in the mechanical, electrical or other systems, which may cause errors.

Using the bite block 18 as a means for securing the position marker 4 as described above is suitable for dental diagnosis and treatment. However, an appropriate means should be used to secure the position marker 4 in accordance with the circumstances. In the case when this apparatus is used for otolaryngologic diagnosis and treatment, for example, a desired purpose can be attained by securing the position marker 4 close to a ear of the patient with adhesive tape or the like.

Next, in the radiographing apparatus shown in FIG. 2, concrete examples of structures provided with both partial CT radiographing and panoramic radiographing functions, control circuits and the like will be described.

The lift frame 14 is movable in the vertical direction as described referring to FIG. 2. This movement in the vertical direction is carried out by using a lift control motor 40 built in the lift frame 14. The horizontal arm 15 is moved in the vertical direction together with the lift frame 14. Between the horizontal arm 15 and the rotary arm 16, a plane movement mechanism 20 is installed. The plane movement mechanism 20 is provided with an X-Y table comprising an X-axis table attached to the horizontal arm 15 and being movable in the front-to-back direction (from lower right to upper left in FIG. 2) with respect to the horizontal arm 15 and a Y-axis table attached to the X-axis table so as to be movable in the lateral direction (from lower left to upper right in FIG. 2) perpendicular to the front-to-back direction. The rotary arm 16 is supported by a rotation shaft 22 rotatably provided in the Y-axis table.

The plane movement mechanism 20 is provided with an X-axis control motor 42 and a Y-axis control motor 44. By driving these motors, the rotary arm 16 can be moved in the front-to-back and right-to-left directions on a horizontal plane. Furthermore, the plane movement mechanism 20 is provided with a rotation control motor 46 for rotating the rotary arm 16. In the case of radiographing by CT scanning, the plane movement mechanism 20 is used to set the rotation center position of the rotary arm 16 before radiographing. In the case of panoramic radiographing, the plane movement mechanism 20 is used to set the rotation center position before radiographing and to sequentially move the rotation center position along a predetermined locus until the end of radiographing.

The X-ray source 1 provided at one end of the rotary arm 16 is equipped with a primary slit selection means 1a, and the two-dimensional X-ray image pickup portion 2 provided at the other end thereof is equipped with an image sensor 2a and a secondary slit selection means 2b. The primary slit selection means 1a is provided with a primary slit width control motor 52 and a primary slit height control motor 56. By driving these motors, the width and height of the X-ray beam emitted from the X-ray source 1 are restricted to prevent unnecessary X-rays from being applied to the object. Furthermore, the secondary slit selection means 2b is provided with a secondary slit width control motor 54, and a secondary slit height control motor 58 By driving these motors, the width and height of the X-ray beam entering the image sensor 2a is restricted to prevent unnecessary X-rays from entering the image sensor 2a. When one of the CT scanning or panoramic radiographing mode is selected, the width and height of each slit are set automatically so as to become a slit opening corresponding to the selected mode.

Figure 8:
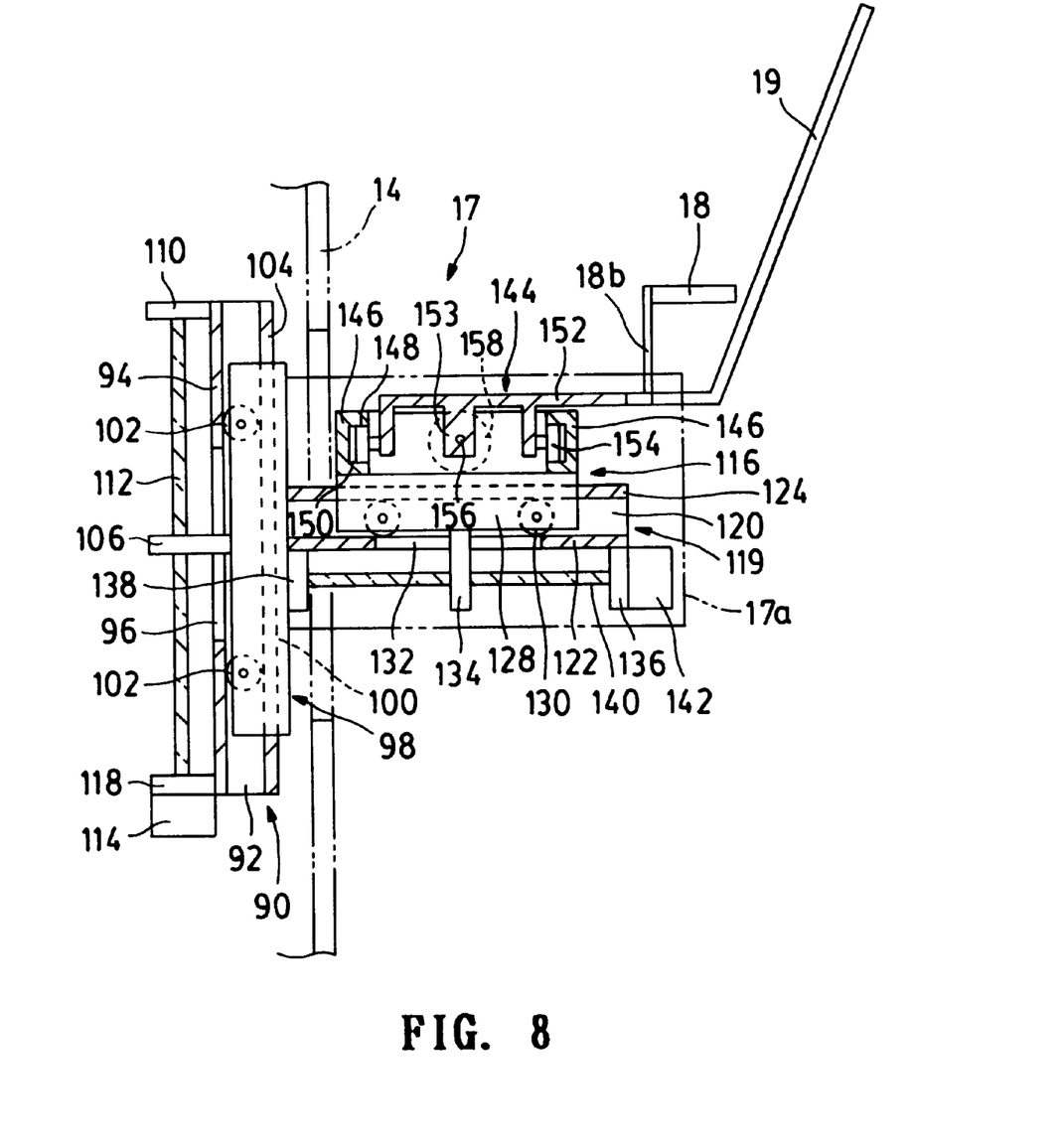
FIG. 8 is a sectional view showing the object position adjustment mechanism of the apparatus in accordance with the embodiment.

The object position adjustment mechanism 17 is configured as shown in FIG. 8. More specifically, a guide frame 90 is provided in the lift frame 14 of the apparatus body 11. This guide frame 90 has a pair of side wall portions 92 (one of them is shown in FIG. 8) disposed in the lateral direction (perpendicular to the surface of the paper in FIG. 8) with a clearance therebetween. Between the pair of the side wall portions 92, a connection wall portion 94 is provided, and at the central portion thereof, a narrow slot 96 extending in the vertical direction is formed. Furthermore, between the side wall portions 92, a first movement table 98 is provided so as to be movable in the vertical direction. This table 98 is provided with a first table body 100 having a rectangular shape. A pair of rollers 102 is used, each rotatably provided at each end portion of the table body 100. Moreover, the side wall portions 92 used in a pair are provided with a pair of guide wall portions 104 (one of them is shown in FIG. 8) with a predetermined clearance from the connection wall portion 94. The above-mentioned rollers 102 are rotatably accommodated between the connection wall portion 94 and the guide wall portions 104.

At the central portion of the first table body 100, a block member 106 extending through the slot 96 of the connection wall portion 94 is provided. Furthermore, at both the upper and lower ends of the connection wall portion 94, mounting members 110, 118 are secured. Between the mounting members 110, 118, a screw shaft 112 is rotatably supported, and a block member 106 is threadedly engaged to the screw shaft 112. A Z-axis control motor 114 is connected to the lower end of the screw shaft 112 passing through the mounting member 118. By driving the motor 114, the first movement table 98 is moved in the vertical direction.

The first movement table 98 is provided with a second movement table 116 so that the table 116 is movable in the front-to-back direction (in the right-to-left direction in FIG. 8). A guide frame 119 is secured to the outer surface of the first table body 100. This guide frame 119 has a pair of side wall portions 120 (one of them is shown in FIG. 8) disposed in the lateral direction with a clearance therebetween. A connection wall portion 122 is provided between the pair of the side wall portions 120, and each of the side wall portions 120 is provided with a guide wall portion 124. The second movement table 116 is movable between the side wall portions 120 in the front-to-back direction. The table 116 is provided with a second table body 128 having a rectangular shape. A pair of rollers 130 is used, each rotatably provided at each end of the second table body 128. The rollers 130 are rotatably accommodated between the connection wall portion 122 and the pair of the guide wall portions 124.

Just as the first movement table 98, the second table body 128 is provided with a block member 134 extending through a slot 132 formed in the connection wall portion 122. This block member 134 is threadedly engaged with a screw shaft 140 rotatably supported between mounting members 136, 138 provided on the connection wall portion 122. An X-axis axis control motor 142 is connected to one end of the screw shaft 140 passing through the mounting member 136. By driving the motor 142, the second movement table 116 is moved in the front-to-back direction.

In addition, the second movement table 116 is provided with a third movement table 144 so as to be movable in the lateral direction (perpendicular to the surface of the paper in FIG. 8). On the upper surface of the second table body 128, a pair of guide members 146 is secured in the front-to-back direction with a clearance therebetween. Each of the guide members 146 is provided with a pair of guide wall portions 148, 150 with a predetermined clearance therebetween. The third movement table 144 is provided with a third table body 152 having a rectangular shape. A pair of rollers 154 is used, each provided at each end of the table body 152. The rollers 154 are rotatably accommodated between the guide wall portions 148, 150.

The third table body 152 is provided with a block member 153. Just as in the case of the second movement table 116, a screw shaft 156 is rotatably supported between mounting members (not shown) provided on the second table body 128, and the block member 153 is threadedly engaged with the screw shaft 156. A Y-axis control motor 158 is connected to one end of the screw shaft 156. By driving the motor 158, the third table body 152 is moved in the lateral direction.

The base portion of the support rod 18b of the bite block 18 and the base portion of the ear rod 19 are secured to the third table body 152. A slot is formed at the front end of the protection cover 17a of the object position adjustment mechanism 17 mounted on the first table body 100, and the bite block 18 and the ear rods 19 project in the upper forward direction through this slot. With this configuration, by driving the above-mentioned motors 114, 142 and 158 using a control means 170 described below, the bite block 18 and the ear rods 19 are moved in the vertical, front-to-back and right-to-left directions, whereby the patient, i.e., an object, can be positioned in a predetermined radiographing area.

Figure 7:
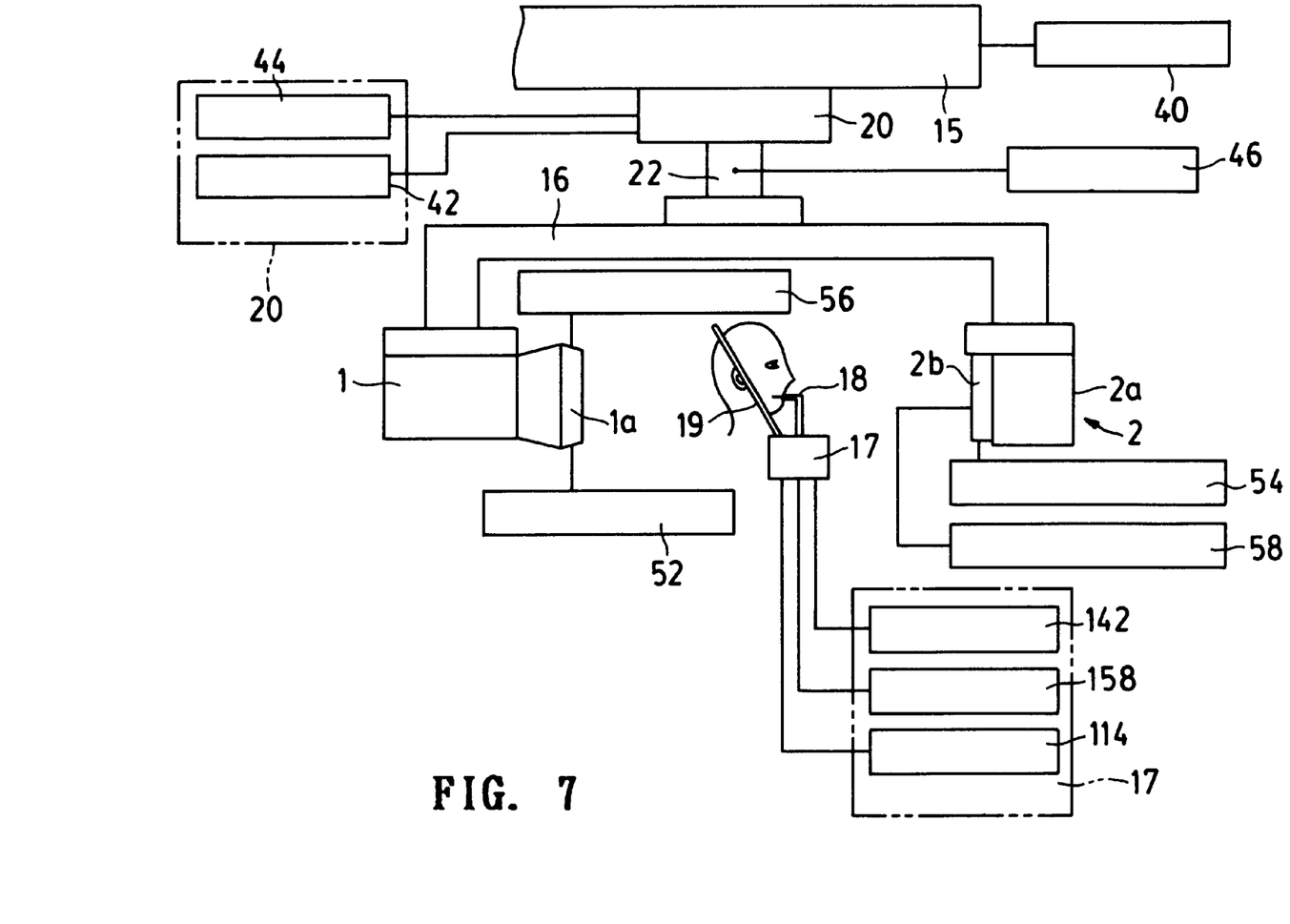
FIG. 7 is a block diagram showing the outline configuration of the main portion and the control circuits of the apparatus in accordance with the embodiment.
Figure 9:
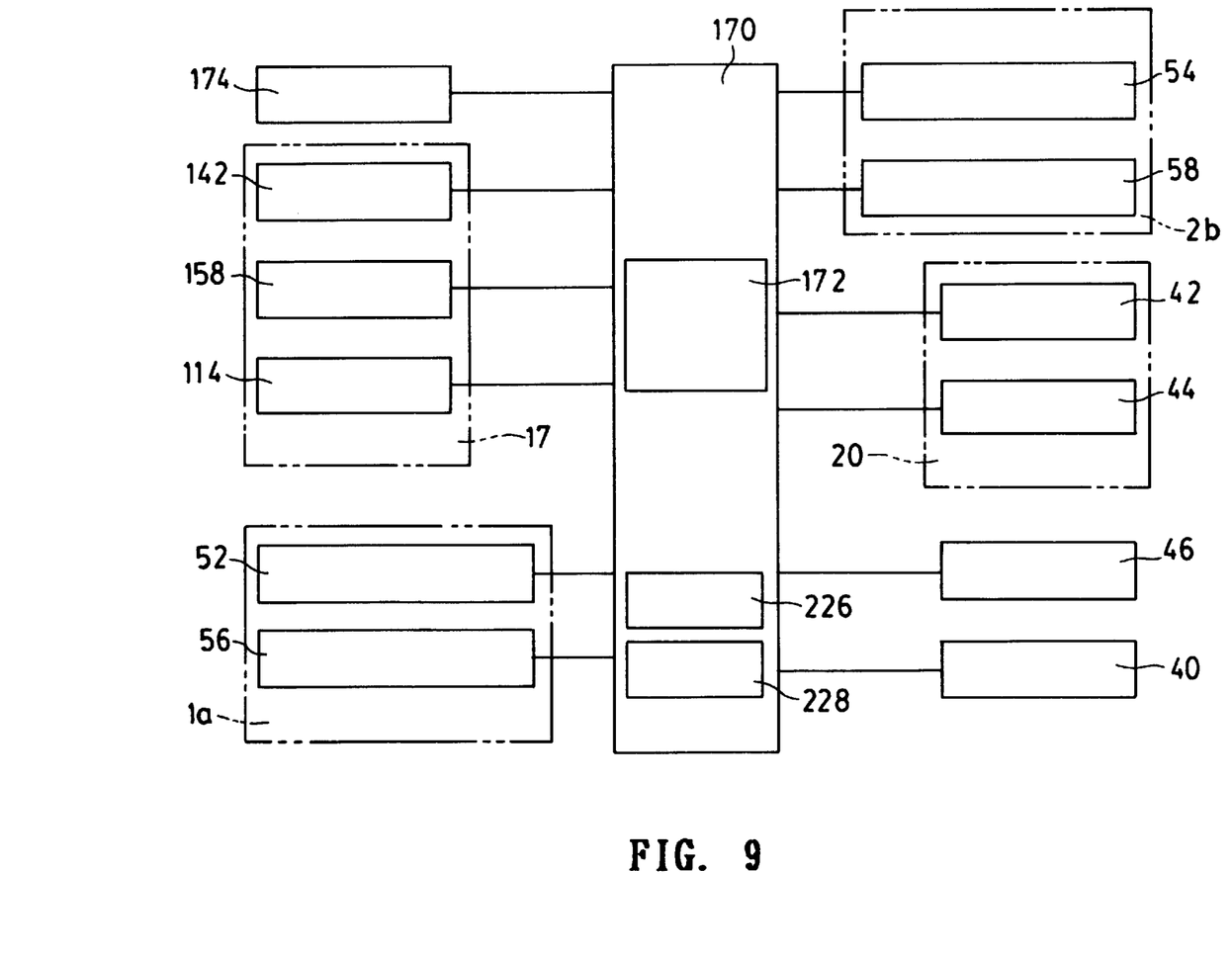
FIG. 9 is a block diagram showing the motor control system of the apparatus in accordance with the embodiment.
Figure 10:
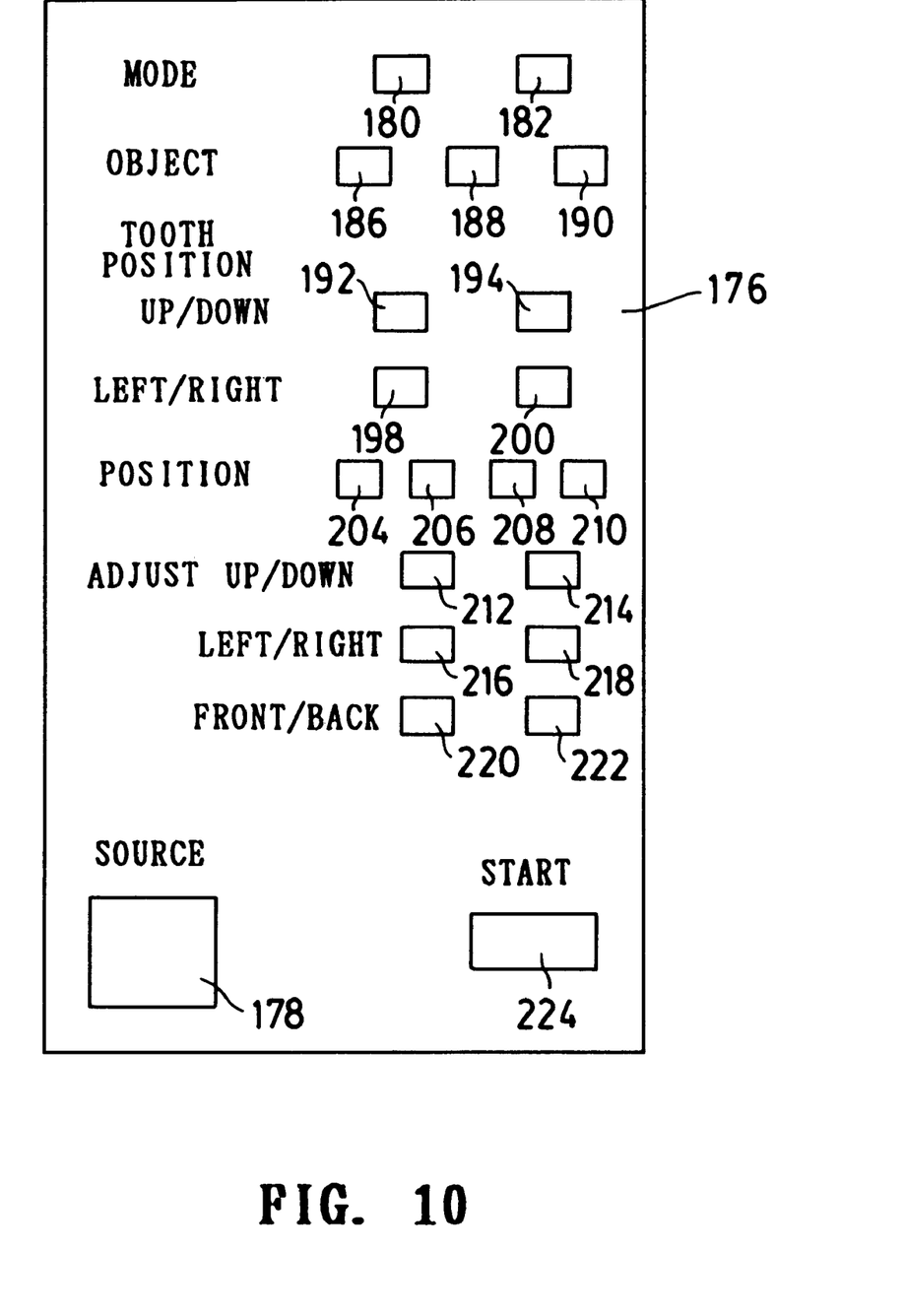
FIG. 10 is a front view showing the operation panel of the apparatus in accordance with the embodiment.

Stepping motors. for example, are used for the motors shown in FIGS. 7 and 8. The operations of the motors are controlled by the control means 170 of the radiographing apparatus as shown in FIG. 9. The control means 170 comprises a microprocessor, for example, and carries out control on the basis of input signals from input means 174. FIG. 10 shows an example of an operation panel 176 constituting a part of the input means 174. Various signals are delivered in accordance with the operations of the switches on the operation panel 176 so that the following operations can be carried out.

Referring to FIG. 10, a switch 178 disposed at the lower left portion is the power switch of the radiographing apparatus. Each time this switch is pressed, on/off operation is repeated. Switches 180, 182 disposed at the top portion are radiographing mode selection switches. When the switch 180 is pressed, the partial CT scanning mode is selected. When the switch 182 is pressed, the panoramic radiographing mode is selected. The switches 186, 188 and 190 disposed therebelow are object selection switches and used in combination with tooth position selection switches 192 to 210 disposed therebelow so that the bite block 18 can be positioned at a predetermined position corresponding to a radiographing mode and a portion to be radiographed.

The switch 186 is pressed when the object is an infant, the switch 188 is pressed when the object is a child, and the switch 190 is pressed when the object is an adult. Furthermore, the switch 192 is pressed when a tooth (or teeth) of the upper jaw is radiographed, and the switch 194 is pressed when a tooth (or teeth) of the lower jaw is radiographed. The switch 198 is pressed when a tooth (or teeth) on the left side is radiographed, and the switch 200 is pressed when a tooth (or teeth) on the right side is radiographed. Furthermore, the switches 204 to 210 are used to specifically determine the position of a tooth (or teeth) to be radiographed. The switch 204 is pressed when the first or second tooth from the center line of the dental arch is radiographed, the switch 206 is pressed when the third or fourth tooth is radiographed, the switch 208 is pressed when the fifth or sixth tooth is radiographed, and the switch 210 is pressed when the seventh or eighth tooth is radiographed. In accordance with these operations, the bite block 18 is placed at a predetermined position. Switches 212 to 222 disposed therebelow are used to fine-adjust the position of the bite block 18. The switches 212, 214 are used to fine-adjust the position in the vertical direction, the switches 216, 218 are used to fine-adjust the position in the right-to-left direction, and the switches 220, 222 are used to fine-adjust the position in the front-to-back direction. A switch 224 disposed at the lower right portion is a radiographing start switch to be pressed after the above-mentioned various settings are completed. When this switch is pressed, X-ray irradiation to the object starts, and radiographing is carried out.

The control means 170 is provided with an operation control means 172 for driving the motors in accordance with a radiographing mode before radiographing or during radiographing, a bite block position storage means 226 and a processing information storage means 228 for storing a variety of information for the above-mentioned operations. In other words, in accordance with the operations of the above-mentioned switches, the motors in the object position adjustment mechanism 17 and the plane movement mechanism 20 are driven, and the motors of the primary slit selection means 1a and the secondary slit selection means 2b are driven, whereby various settings are carried out. In addition, when radiographing starts, the rotation control motor 46 is driven, and the rotary arm 16 is rotated. In the case of panoramic radiographing, the motors of the plane movement mechanism 20 are also driven.

Figure 11:
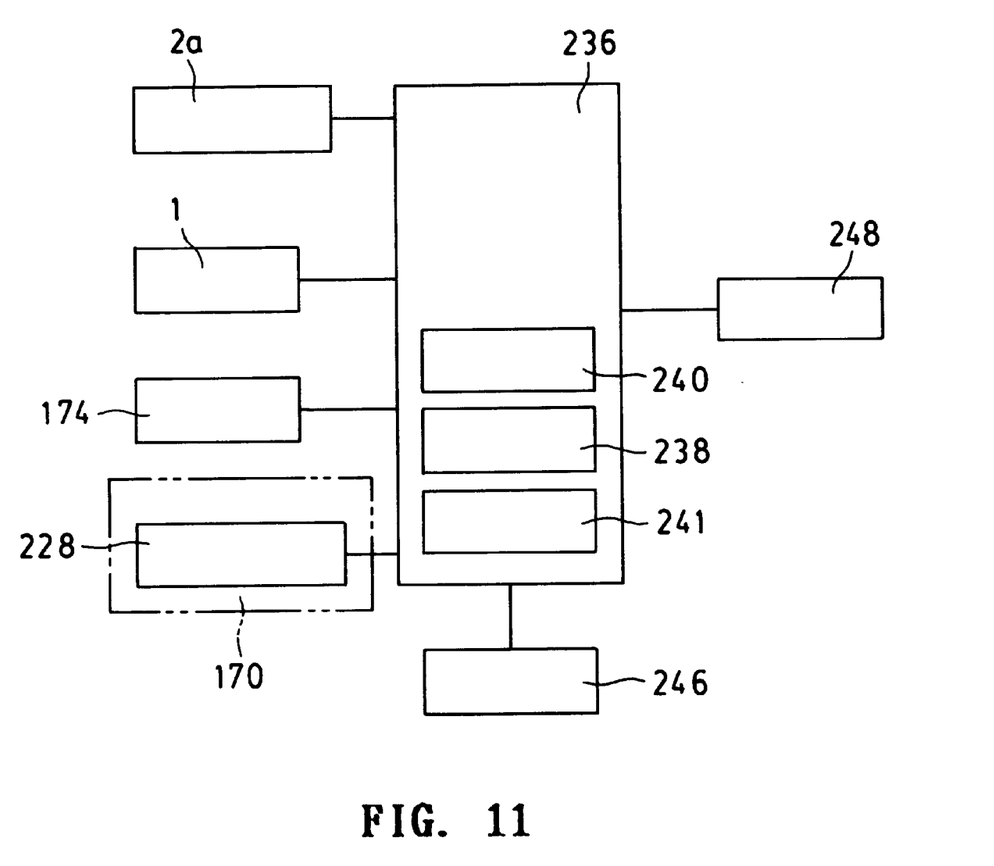
FIG. 11 is a block diagram showing the image signal processing system of the apparatus in accordance with the embodiment.

An X-ray image picked up by the above-mentioned control is processed by an image signal processing system shown in FIG. 11 to obtain a desired two-dimensional X-ray image. An image signal processing means 236 comprises an image processing microprocessor, for example, and further comprises an A/D conversion means 238, a frame memory 240, an image memory 241 for computing and the like. An image signal detected by the image sensor 2a and sent to the image signal processing means 236 is converted into a digital signal by the A/D conversion means 238, and stored in the frame memory 240 as plural two-dimensional images. The plural two-dimensional images are read by the image memory 241 for computing and processed by using the information stored in the processing information storage means 228, whereby a tomographic image is generated. This tomographic image is displayed on a display means such as a liquid crystal display, and stored in a storage device of an external computer or in an external storage means 246, such as a hard disk or an optical disk.

In the case of the present invention in particular, the processing procedure shown in FIG. 6 has been stored in the processing information storage means 228. The position of the center of gravity of the image of the position marker 4 is obtained, and a correction amount is calculated from the position of the center of gravity. By using this correction amount, the two-dimensional X-ray image is corrected to build a desired CT image.

Although the above-mentioned embodiment is provided with both the plane movement mechanism 20 and the object position adjustment mechanism 17, position adjustment before radiographing can be accomplished by using one of the mechanisms in principle. In the case of partial CT scanning in particular, no problem occurs in actual operation when only the object position adjustment mechanism 17 is used. Therefore, the plane movement mechanism 20 can be omitted to reduce cost. Furthermore, instead of directly adjusting the position of the patient's head used as an object by using the object position adjusment mechanism 17 just as in the case of the above-mentioned embodiment, it is possible to adopt a structure wherein an X-Y-Z three-direction drive means is provided in a chair for the patient and the head of the patient is secured to the chair. This simplifies the configuration of the entire apparatus.

Figure 12:
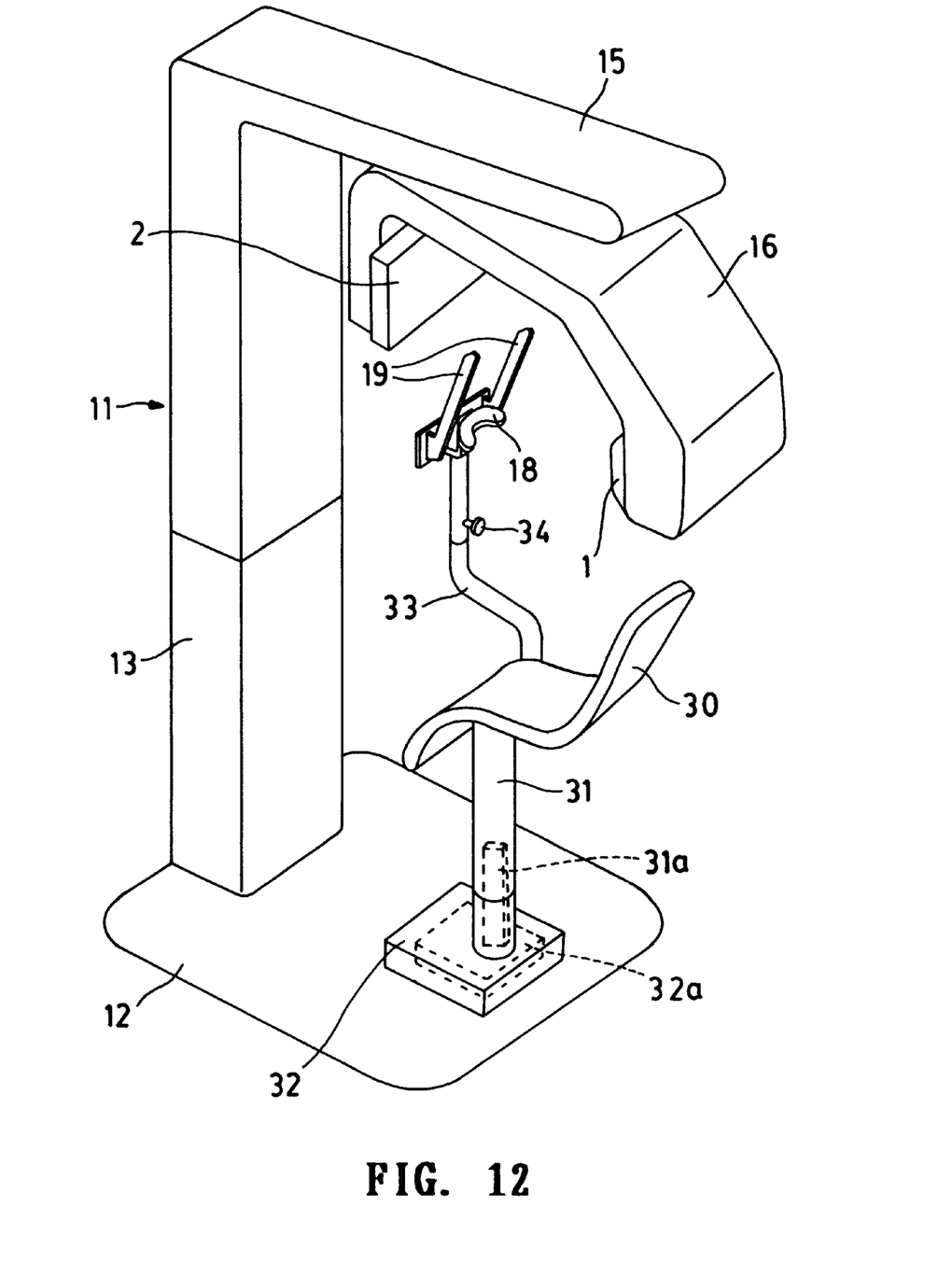
FIG. 12 is a perspective overall view showing a modified example of the apparatus in accordance with the embodiment.

FIG. 12 is a view showing an example wherein an X-Y-Z three-direction drive means is provided in a chair as described above. The column 31 of a chair 30 is supported by a support base 32 having an X-Y table 32a built therein. In addition, a vertical movement mechanism 31a is built in the column 31 so that the chair 30 can be moved on the whole in the X-Y-Z three directions. Furthermore, a bite block 18 and ear rods 19 are provided at the end of a support arm 33 projecting upward from the chair 30, and the support arm 33 is provided with a screw portion 34 for height adjustment. Such an appropriate configuration as that of the object position adjustment mechanism 17 shown in FIG. 8 for example may be adopted for the X-Y table 32a of the support base 32 and the vertical movement mechanism 31a of the column 31. By using this kind of configuration, it is possible to omit the object position adjustment mechanism 17 shown in FIG. 2 and the plane movement mechanism 20 shown in FIG. 7.

In addition, the control circuits including the control means 170, the image signal processing means 236 and the like are provided at appropriate positions in the apparatus body 11 as necessary. The operation panel 176 and the display means 248 are disposed on the back side of the lift frame 14, for example. Furthermore, the control circuits may be integrated with the operation panel 176 and the display means 248 as a unitary control device, and this device may be installed on the back side of the lift frame 14, for example, or away from the apparatus body 11 and close to the operator for easy operation.

Moreover, although the X-ray source 1 and the X-ray image pickup portion 2 are rotated 360 degrees in the description of the above-mentioned embodiment, the image pickup system comprising these may be rotated less than 360 degrees, and should only be rotated in an ordinary range required for desired radiographing.

What is claimed is:

1. A CT scanning apparataus comprising an image pickup system having an X-ray source being rotated along a circular orbit around an object and a two-dimensional X-ray image pick portion disposed opposite to said X-ray source with a direction of X-ray radiation extending from said X-ray surce to said image pickup portion and with said object therebetween and being rotated along a circular orbit, and being configure to rotate said image pick up system so as to radiograph three-dimensional areas inside said object, said apparatus further comprising a substance capable of being detected as an X-ray image used as a position marker, said position marker being disposed so as to be positioned in the image pickup view of said image pickup system during the rotation of said image pickup system and radiographed together with said object, means for calculating a correction amount for each X-ray image from the position of the image of said position marker in an obtained two-dimensional X-ray image on a plane perpendicular to said direction of X-ray irradiation, a means for correcting said two-dimensional X-ray image by using said correction amount, and a means for building a CT image from said corrected two-dimensional X-ray image whereby image quality of the two-dimensional X-ray image is improved.

2. A CT scanning apparatus in accordance with claim 1, wherein said position marker has a shape being symmetrical with respect to the center line thereof.

3. A CT scanning apparatus in accordance with claim 1 or 2, further comprising a means for securing said position marker to said object.

4. A CT scanning apparatus in accordance with claim 3, further comprising a mounting means for securing said position marker to a bite block.

5. A CT scanning apparatus in accordance with claim 4, wherein said mounting means for securing said position marker has a mechanism capable of removably or movably securing said position marker to said bite block.

6. A CT scanning apparatus in accordance with claim 1 or 2, wherein said X-ray source and said image pickup portion rotate along circular orbits on a horizontal plane.

7. A CT scanning apparatus comprising an image pickup system having an X-ray source being rotated along a circular orbit around an object and a two-dimensional X-ray image pickup portion disposed opposite to said X-ray source with a direction of X-ray radiation extending from said X-ray source to said image pickup portion and with said object therebetween and being rotated along circular orbit, and being configured to rotate said image pickup systems so as to radiograph three-dimensional areas inside said object, and a chair or a patient with a means for securing the patient's head used as an object, wherein said chair is movable at least in the front to back and right to left directions, wherein a substance capable being detected as an X-ray image is used as a position marker, said position marked is disposed so as to be positioned in the image pickup view of said image pickup system during the rotation of said image pickup system and radiographed toghether with said object, a correction amount for each X-ray image is calculated from the position of the image of said position marker in an obtained two-dimensional X-ray image, said two-dimensional X-ray images corrected by using said correction amount, and a CT image is built.

8. A CT scanning apparatus comprising a image pickup having an X-ray source being rotated along a circular orbit around an object and a two dimensional X-ray image pickup portion disposed opposite to said X-ray source with a direction of X-ray radiation extend from said X-ray source to said image pickup portion and with said object therebetween and being rotated along a circular orbit, and being configured to rotate said image pickup system so as to radiograph three-dimensional areas inside said object, said apparatus further comprising a substance capable of being detected as an X-ray image used as a position marker, said position marker being disposed so as to be positioned in the image pickup view of said image pickup system during the rotation of said image pickup system and radiographed, and error data regarding said image pickup system in each X-ray image is calculated from the position of the image of said position marker in an obtained two-dimensional X-ray image.

* * * * *